(12) United States Patent
Arlt

(10) Patent No.: US 9,108,912 B2
(45) Date of Patent: *Aug. 18, 2015

(54) HYDROFORMYLATION PROCESS

(75) Inventor: Dieter Arlt, Rinteln (DE)

(73) Assignee: UMICORE AG & CO. KG, Hanau-Wolfgang (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/122,153

(22) PCT Filed: May 25, 2012

(86) PCT No.: PCT/EP2012/059841
§ 371 (c)(1),
(2), (4) Date: Apr. 23, 2014

(87) PCT Pub. No.: WO2012/163831
PCT Pub. Date: Dec. 6, 2012

(65) Prior Publication Data
US 2014/0243558 A1    Aug. 28, 2014

(30) Foreign Application Priority Data

May 27, 2011 (DE) .......................... 10 2011 102 666
Aug. 16, 2011 (DE) .......................... 10 2011 110 621

(51) Int. Cl.
| | |
|---|---|
| C07C 45/50 | (2006.01) |
| C07C 43/13 | (2006.01) |
| B01J 31/24 | (2006.01) |
| C07F 9/50 | (2006.01) |
| C07F 15/00 | (2006.01) |
| C07C 43/178 | (2006.01) |
| B01J 31/22 | (2006.01) |

(52) U.S. Cl.
CPC ........... *C07C 45/505* (2013.01); *B01J 31/2208* (2013.01); *B01J 31/2414* (2013.01); *C07C 43/135* (2013.01); *C07C 43/1788* (2013.01); *C07C 45/50* (2013.01); *C07F 9/5027* (2013.01); *C07F 15/008* (2013.01); *C07F 15/0073* (2013.01); *C07C 2101/04* (2013.01); *C07C 2531/24* (2013.01)

(58) Field of Classification Search
None
See application file for complete search history.

(56) References Cited

U.S. PATENT DOCUMENTS

| | | | |
|---|---|---|---|
| 4,064,145 A | 12/1977 | Taylor | |
| 4,215,077 A | 7/1980 | Matsumoto et al. | |
| 4,238,419 A | 12/1980 | Matsumoto et al. | |
| 4,678,857 A | 7/1987 | Dureanleau et al. | |
| 5,290,743 A | 3/1994 | Chang | |
| 7,279,606 B1 | 10/2007 | White | |
| 7,294,602 B1 | 11/2007 | White | |
| 7,655,821 B1 | 2/2010 | White | |
| 8,791,305 B2 * | 7/2014 | Arlt .............................. | 568/454 |
| 2010/0292514 A1 * | 11/2010 | White ............................ | 568/454 |

FOREIGN PATENT DOCUMENTS

| | | |
|---|---|---|
| WO | 2008/121194 A1 | 10/2008 |
| WO | 2010/132087 A1 | 11/2010 |
| WO | 2012/163837 A1 | 12/2012 |

OTHER PUBLICATIONS

Boogaerts, et al. (2010) "High chemo and regioselective formation of alcohols from the hydrocarbonylation of alkenes using cooperative ligand effects" Chem. Commun., 46, 2194-2196.
International Search Report for Application No. PCT/EP2012/059841, mailed Jul. 18, 2012 (in English).

* cited by examiner

*Primary Examiner* — Brian J Davis
(74) *Attorney, Agent, or Firm* — Smith, Gambrell & Russell, LLP

(57) ABSTRACT

The present invention relates to a process for producing 4-hydroxybutyraldehyde, characterized in that allyl alcohol dissolved in polar solvents is reacted with CO and $H_2$ in the presence of a catalytic system which is formed from a rhodium complex and a cyclobutane ligand which contains at least two trans-coordinated 3 5-dialkylphenylphosphinomethyl groups, with the exclusion of catalysts which contain an aliphatic, araliphatic or cycloaliphatic phosphine as ligand.

11 Claims, No Drawings

HYDROFORMYLATION PROCESS

The present invention relates to a process for hydroformylating allyl alcohol in order to produce 4-hydroxybutyraldehyde.

BACKGROUND OF THE INVENTION

The hydroformylation of allyl alcohol is known and is utilized industrially (see e.g. U.S. Pat. Nos. 4,064,145; 4,215,077; 4,238,419; 4,678,857; 5,290,743). Allyl alcohol is reacted in these processes with $CO/H_2$ gas mixtures, giving 4-hydroxy-butyraldehyde (HBA). Following distillative removal of undesired by-products, HBA is hydrogenated in a known manner to give 1,4-butanediol (BDO).

A disadvantage of this mode of production is the formation of undesired by-products. In particular, as well as the desired linear product, the isomeric branched product 3-hydroxy-2-methylpropionaldehyde (HMPA) and other $C_3$ by-products such as n-propanol and propionaldehyde are formed. This adversely affects the economic viability of the process.

The present invention provides a process for producing 4-hydroxybutyraldehyde, characterized in that ally alcohol dissolved in polar solvents is reacted with CO and $H_2$ in the presence of a catalytic system which is formed from a rhodium complex and a cyclobutane ligand which contains at least two trans-coordinated, 3,5-dialkylphenyl-phosphinomethyl groups, with the exclusion of catalysts which contain an aliphatic, araliphatic or cycloaliphatic phosphine as ligand.

DETAILED DESCRIPTION OF THE INVENTION

Trans-1,2-(3,5-dialkylphenylphosphinomethyl)cyclobutanes which are used as ligands in the present invention have the formula [A]

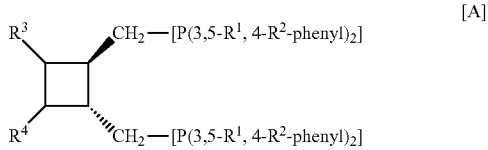

in which
$R^1$ is alkyl, preferably methyl, ethyl or propyl
$R^2$ is H or an alkoxy group,
$R^3$ and $R^4$, independently of one another, are H, $CH_2OR^1$, $CH_2O$-aralkyl, $CH_2OH$, $CH_2$—$[P(3,5-R^1,4-R^2\text{-phenyl})_2]$ or $CH_2O$—$(CH_2$—$CH_2$—$O)_m$—H where m is a number from 1 to 1000.

Preferably [A] is an all-trans-cyclobutane derivative.

An additional aspect of the invention is the use of novel catalysts of the formula [A] which permit different embodiments of the process according to the invention.

Usually, the hydroformylation of allyl alcohol with known catalysts is carried out in homogeneous phase. After the reaction, HBA, HMPA and other by-products are separated off from the catalyst by extraction with water.

The hydroformylation according to the invention in polar solvents allows lipophilic catalysts of the formula [A] to be separated off by extraction with hydrophobic solvents, and the catalyst to be returned to the first process stage.

Novel hydrophilic catalyst systems of the formula [A] with polyether groups can be used in membrane reactors and thus allow the process products to be separated off continuously after the hydroformylation.

The process according to the invention differs with respect to hitherto described processes for producing HBA by virtue of the exclusion of catalysts which contain ligands of the formulae $PR'_3$, where R' is an aliphatic, araliphatic or cycloaliphatic radical. Catalysts of this type hydrogenate a considerable fraction of the allyl alcohol used to give undesired by-products (see U.S. Pat. No. 7,655,821 B1).

By contrast, in the process according to the invention, instead of catalysts which contain a cyclobutane ligand which has at least two trans-coordinated 3,5-dialkylphenylphosphino-methyl groups, it is also possible to use diphosphines of the DIOP series, such as e.g.2,3-O-isopropylidene-2,3-dihydroxy-1,4-bis[bis(3,5-dimethylphenylphosphino]butane; (see WO2010/132087).

However, preference is given to catalysts of the cyclobutane series, which allow more favorable HBA:HMPA- proportions to be achieved.

The polar solvents used in the process according to the invention are not reactive toward the products of the hydroformylation. In contrast to the solvents used in known processes, (see e.g. WO2010/132087), they are soluble in significant proportions, and sometimes also completely, in water.

Polar solvents which may be mentioned are, for example, ethanol, propanol, n-butanol, isobutanol, 1,4-butanediol and polyethers of the formula $CH_3O$—$(—CH_2$—$CH_2$—$O)_n$—H with a molecular weight >2000.

The hydroformylation takes place under reaction conditions known per se in the temperature range from 20 to 120° C. and in a pressure range from 2-20 bar. The optimum performance is ascertained by appropriate preliminary experiments depending on the predetermined equipment.

The molar ratio of $CO:H_2$ is ca. 1:1, but can vary considerably depending on the embodiment.

The reaction time is 0.5-4 hours. At the start of the reaction, the allyl alcohol concentration is 5-50%, preferably 10-25%, based on the solvent or solvent mixture.

HBA (and HMPA) are hydrogenated in a manner known per se to give the corresponding dihydroxy compounds, and fractional distillation of the crude product gives the desired 1,4-butanediol in pure form. Ni, Co, Ru, Pt, Pd, Cu, Zn and Cr catalysts can be used for the hydrogenation. Raney® Ni catalysts are particularly preferably used. The hydrogenation is generally carried out at temperatures of 60-200° C. and in the pressure range 15-70 bar.

The examples below illustrate the process according to the invention:

EXAMPLE 1

Preparation of a novel catalyst which is used in the process according to the invention:
a) Preparation of a novel intermediate from known all-trans-1,2,3,4-(hydroxy-methyl)cyclobutane:

88 mg (0.5 mmol) of all-trans-1,2,3,4-(hydroxymethyl) cyclobutane were dissolved in 3 ml of anhydrous pyridine and, at 0° C., 251 mg (0.9 mmol) of trityl chloride were added with intense stirring. The reaction mixture was kept at 0° C. overnight with stirring. Then, it was added to 10 ml of water and extracted with ethyl acetate (3×5 ml), then dried with $MgSO_4$ and evaporated to dryness in a rotary evaporator.

The crude product was separated off by chromatography (silica gel). (Eluent: ethyl acetate:hexane 1:3→2:3→ethyl acetate:methano 195:5).

The main product obtained was 114 mg (34% of theory) of all-trans-1,2-(hydroxymethyl)-3,4-(trityloxymethyl)cyclo butane.

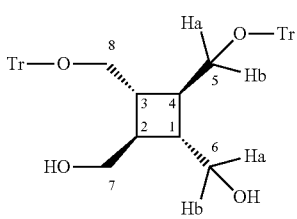

$^1$H-NMR (500MHz, CDCl$_3$): 7.15-7.4 (m, 15H, Ar); 3.86 (m, 2H, H-6a, H-7a); 3.63 (m, 2H, H-6b, H-7b); 3.18 (m, 2H, H-5a, H-8a); 2.98 (m, 2H, H-5b, H-8b); 1.84 (m, 4H, H-1, H-2, H-3 and H-4);
$^{13}$C-NMR (CDCl$_3$): 143.95; 128.60; 127.79; 126.98; 86.84; 66.24; 65.71; 43.68; 39.06.

b) In a manner known per se, this compound was tosylated and reacted with LiP(3,5-xylyl)$_2$.

EXAMPLE 2

Hydroformylation corresponding to the process according to the invention:

In 4 ml of dried and degassed tert-butyl methyl ether, 16 mmol of all-trans-1,2,3,4-(3,5-xylylphosphinomethyl)cyclobutane are reacted under argon with [Rh(CO)$_2$(acac)] (8 mmol).

The resulting solution is injected into an autoclave under argon and flushed with a CO:H$_2$-1:1 mixture. Via a side arm, a solution of 1 ml of allyl alcohol in 15 ml of ethanol is then added and the reaction is carried out at a pressure of 40 bar and a temperature of 120° C. This gives 97% of theory of HBA+ HMPA in a ratio of ca. 14:1.

The invention claimed is:

1. A process for producing 4-hydroxybutyraldehyde, comprising: reacting allyl alcohol in polar solvents with CO and H$_2$ in the presence of a catalytic system which is formed from a rhodium complex and a cyclobutane ligand which comprises at least two trans-coordinated 3,5-dialkylphenylphosphinomethyl groups, with the exclusion of catalysts which contain an aliphatic, araliphatic or cycloaliphatic phosphine as ligand.

2. The process as claimed in claim 1, wherein the cyclobutane ligand is selected from the group consisting of all-trans-1,2,3,4-(3,5-xylylphosphino-methyl) cyclobutane, trans-1,2-(3,5-xylylphosphino-methyl)cyclobutane, all-trans-1,2,3 -(3,5-xylylpho-sphino-methyl)-4-(methoxymethyl)cyclobutane, all-trans-1,2-(3,5-xylylphosphino-methyl)-3,4-bis(trityloxymethyl)cyclobutane, all-trans-1,2,3 -(3,5-xylylphosphino-methyl)-4-(hydroxymethyl)cyclobutane, and all-trans-[1,2,3 -(3,5-xylylphosphino-methyl)-4-CH$_2$—(O—CH$_2$—CH$_2$—O)$_m$—H]-cyclobutane, where m is a number from 1-1000.

3. The process as claimed in claim 1, wherein alcohols in which water is soluble to at least 2% parts by weight, are used as polar solvents.

4. The process as claimed in claim 1, wherein polyethers which are water-soluble and whose molecular weight is >2000 are used as polar solvents.

5. All-trans-1,2-(hydroxymethyl)-3,4-(trityloxymethyl) cyclobutane.

6. The process as claimed in claim 1, wherein the catalytic system is formed from a rhodium complex and all-trans-[1,2,3-(3,5-xylylphosphino-methyl)-4-CH$_2$—(O—CH$_2$—CH$_2$—O)$_m$—H]-cyclobutane, where m is a number from 1-1000 and the hydroformylation takes place in a membrane reactor.

7. The process as claimed in claim 1, wherein the catalyst used is separated off from the reaction mixture, optionally after adding water, by extraction with hydrophobic solvents and is reused.

8. The process as claimed in claim 1, wherein the catalytic system is separated off, optionally after adding water, with hydrophobic solvents and is reused.

9. The process of claim 3, wherein alcohols in which water is soluble to at least 5% parts by weight are used as polar solvents.

10. The process of claim 1, wherein the polar solvent is selected from the group consisting of ethanol, propanol, n-butanol, isobutanol, 1,4-butanediol, polyethers of the formula CH$_3$O—(—CH$_2$—CH$_2$—O)$_n$—H with a molecular weight of greater than 2000, and combinations thereof.

11. A catalyst system comprising: a rhodium complex and a cyclobutane ligand selected from the group consisting of all-trans-1,2,3,4-(3,5-xylylphosphino-methyl) cyclobutane, all-trans-1,2,3-(3,5-xylylphosphino-methyl)-4-(methoxymethyl)cyclobutane, all-trans-1,2-(3,5-xylylphosphino-methyl)-3,4-bis(trityloxymethyl)cyclobutane, all-trans-1,2,3-(3,5-xylylphosphino-methyl) -4-(hydroxymethyl) cyclobutane, and all-trans-[1,2,3-(3,5-xylylphosphino -methyl)-4-CH$_2$—(O—CH$_2$—CH$_2$—O)$_m$—H]-cyclobutane, where m is a number from 1-1000.

* * * * *